United States Patent
Chappius

(10) Patent No.: US 6,554,830 B1
(45) Date of Patent: Apr. 29, 2003

(54) FENESTRATED SURGICAL ANCHOR AND METHOD

(75) Inventor: James L. Chappius, Marietta, GA (US)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/545,920

(22) Filed: Apr. 10, 2000

(51) Int. Cl.⁷ .............................................. A61B 17/70
(52) U.S. Cl. ............................ 606/61; 606/73; 606/93
(58) Field of Search ........................ 623/17.11, 17.16; 606/60, 61, 65, 73, 92, 93, 94

(56) References Cited

U.S. PATENT DOCUMENTS 5,743,912 A * 4/1998 Lahille et al. ................. 606/65
6,048,343 A * 4/2000 Mathis et al. ................. 606/72
6,214,012 B1 * 4/2001 Karpman et al. ............. 606/61

OTHER PUBLICATIONS

Brodie E. McKoy and Yuehuei H. An, "An Injectable Cementing Screw for Fixation in Osteoporotic Bone", pp. 216–220.

* cited by examiner

*Primary Examiner*—Cary E. O'Connor
(74) *Attorney, Agent, or Firm*—Woodard, Emhardt, Naughton, Moriarty & McNett LLP

(57) ABSTRACT

Preferably, each anchor incorporates a passage for receiving boding cement therein. The passage communicates with one or more fenestrations or holes, preferably formed at the distal end of the anchor, that allow the bonding cement to pass from and disperse about the anchor. Since at least some of the bonding cement received in the passage passes from the anchor and, preferably, into the material of the skeletal member to which the anchor is engaged, a firm fixation or anchoring of the anchor within the skeletal member is facilitated.

18 Claims, 2 Drawing Sheets

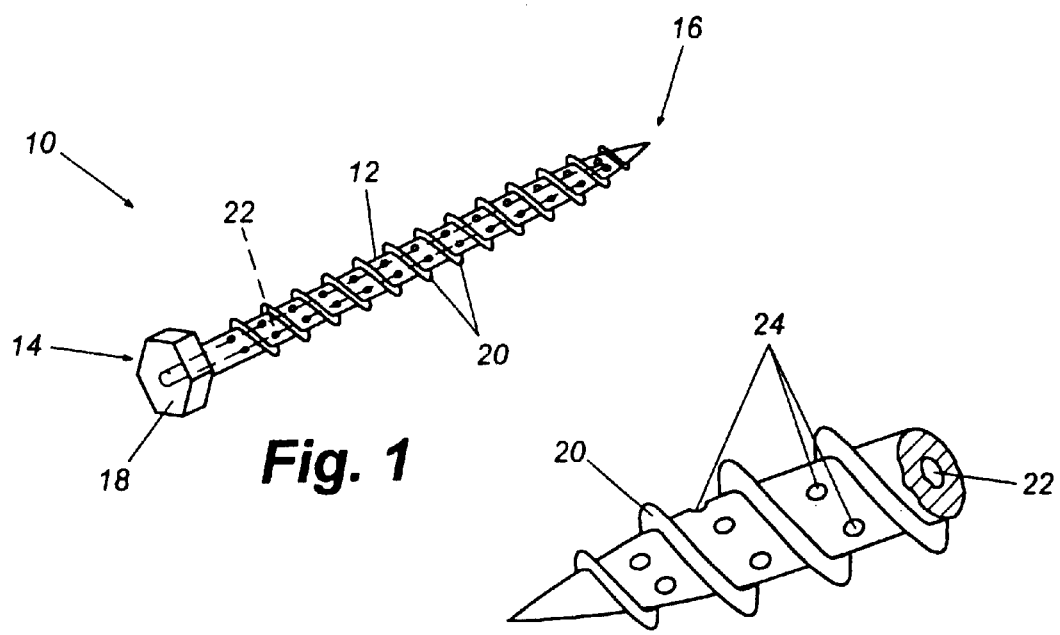
Fig. 1
Fig. 2
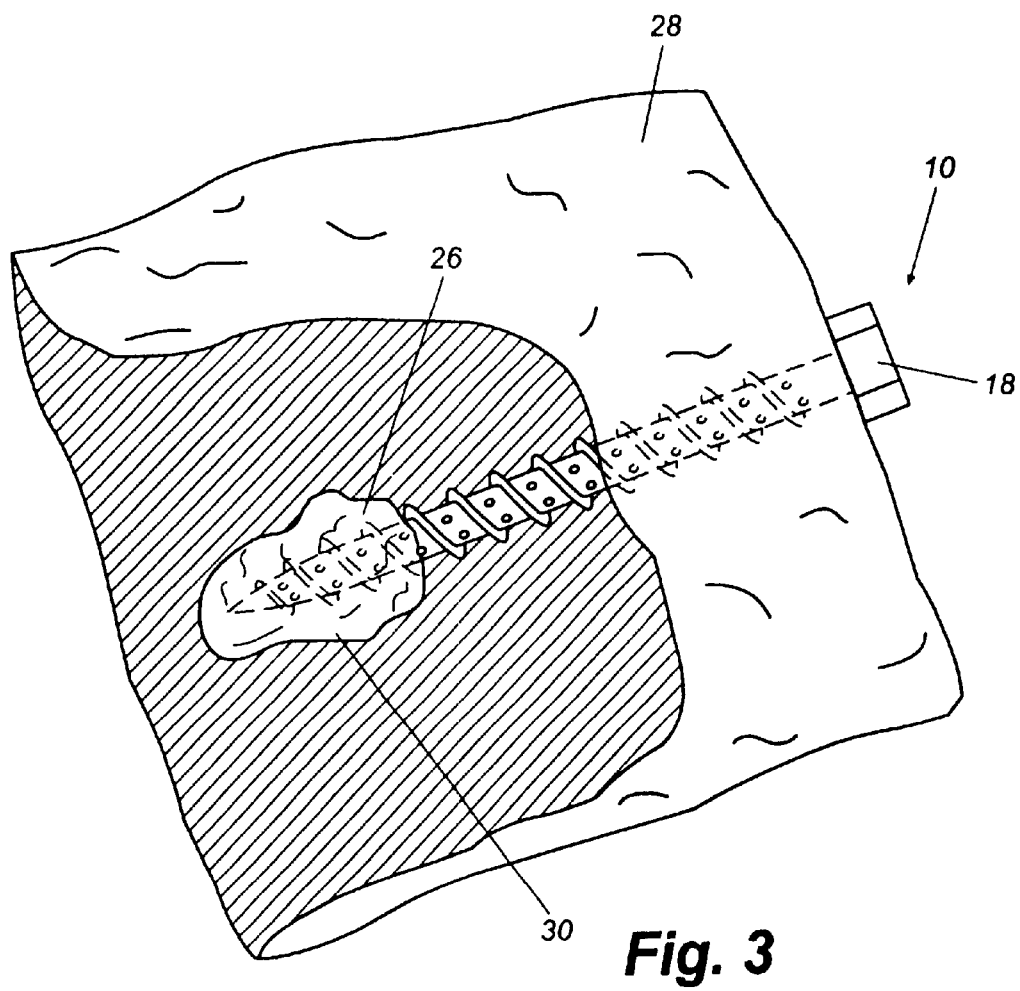
Fig. 3

FENESTRATED SURGICAL ANCHOR AND METHOD

BACKGROUND OF THE INVENTION

1. Field of the Invention

The present invention generally relates to surgical instruments and, in particular, relates to surgical anchors which are configured for securely anchoring within skeletal members, such as vertebrae, for instance.

2. Description of Related Art

Skeletal structures are formed of bones and adjoining structures which include cartilage, for instance. For various reasons, these skeletal structures may require artificial support or stabilization. For example, the human spine is composed of a column of thirty-three bones, called vertebrae, and their adjoining structures. The twenty-four vertebrae nearest the head are separate bones capable of individual movement and generally are connected by anterior and posterior longitudinal ligaments and by discs of fibrocartilage, called intervertbral discs, positioned between opposing faces of adjacent vertebrae. Each of these vertebrae include a vertebral body and a dorsal-arch that enclose an opening, called the vertebral foramen, through which the spinal cord and spinal nerves pass. The remaining nine vertebrae are fused to form the sacrum and the coccyx and are incapable of individual movement.

It is well known in the prior art to utilize pedicle screws for posterior lumbar stabilization procedures. These procedures typically include inserting a pedicle screw posteriorly into the pedicle or pillar of the lumbar spine, and then connecting the screw to either plates or rods for stabilization of the lumbar spine for fractures, tumors and various degenerative conditions. A bone graft also can be added to help solidify the stabilization. When this procedure is used on osteoporotic patients, however, pedicle screw fixation is sometimes difficult to achieve because the threads of the pedicle screw are unable to properly secure within the material of the pillar.

Similar results also may be observed when attempting to secure surgical anchors within the material of other skeletal members.

Therefore, there exists a need for improved surgical anchors which address these and other shortcomings of the prior art.

SUMMARY OF THE INVENTION

Briefly stated, the present invention generally relates to improved surgical anchors which are configured for securely anchoring within skeletal members. In a preferred embodiment, the anchor may be configured as a pedicle anchor which is adapted to be anchored within a vertebrae of a spine, for instance. Preferably, each anchor incorporates a passage, such as a longitudinal bore, for instance, for receiving a medical adhesive or boding cement (i.e., methomathactuloid, cranial plast, etc.) therein. The passage communicates with one or more fenestrations or holes, preferably formed at the distal end of the anchor, that allow the bonding cement to pass from and disperse about the anchor. Since at least some of the bonding cement received in the passage passes from the anchor and, preferably, into the material of the skeletal member, i.e., a vertebral body, a firm fixation or anchoring of the anchor within the vertebral body is facilitated. Due to the dispersion of bonding cement into the material of the vertebral body, and an associated increase in the strength of the vertebral body, such an anchoring of the anchor may be facilitated even though the vertebral body is osteoporotic.

In accordance with an aspect of the present invention, some embodiments may incorporate the use of bonding cement which produces an exothermic reaction during curing. In these embodiments, the hole(s) preferably are arranged along a distal one-third of the elongated body, thereby reducing the tendency of the heat produced during curing of the cement from damaging surrounding nerves and/or tissues.

In accordance with another aspect of the present invention, some embodiments of the surgical anchor may incorporate a plug member which is adapted to cooperate with the proximal end of the elongated body for securing the position of the proximal end within a skeletal member.

In accordance with another aspect of the present invention, a system for lumbar spine stabilization is provided. In a preferred embodiment, the system incorporates a plurality of pedicle anchors, with each of the pedicle anchors being configured to engage and anchor within a pedicle of a lumbar spine. Preferably, each of the pedicle anchors incorporate a proximal end, a distal end, a passage, and at least one hole, with the passage extending at least partially through the pedicle anchor from the proximal end, and the hole(s) extending at least partially through the pedicle anchor and communicating with the passage. A supply of bonding cement also is provided, with each of the pedicle anchors being further configured so that bonding cement is receivable in the passage at the proximal end, deliverable through the passage, through the hole(s) and into the pedicle in which the pedicle anchor is engaged.

In accordance with another aspect of the present invention, a method for anchoring a surgical anchor in a skeletal member is provided. Preferably, the method includes the steps of: (1) providing a surgical anchor having a proximal end, a distal end, a passage, and at least one hole, with the passage extending at least partially through the anchor from the proximal end, and the hole(s) extending at least partially through the anchor and communicating with the passage; (2) inserting the anchor at least partially into the skeletal member so that the hole(s) are at least partially disposed within the skeletal member; and, (3) delivering bonding cement into the passage so that at least a portion of the bonding cement is delivered from the passage, through the hole(s), and into the skeletal member.

Other features and advantages of the present invention will become apparent to one with skill in the art upon examination of the following drawings and detailed description. It is intended that all such additional features and advantages be included herein within the scope of the present invention, as defined by the claims.

BRIEF DESCRIPTION OF THE SEVERAL VIEWS OF THE DRAWINGS

The present invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 1 is a perspective view of a preferred embodiment of the present invention;

FIG. 2 is a cut-away view of the embodiment of FIG. 1, showing detail of the cement dispersion holes;

FIG. 3 is a partially cut-away perspective view of the embodiment of FIGS. 1 and 2 shown anchored within a representative skeletal member.

DETAILED DESCRIPTION OF THE INVENTION

Figure 4:
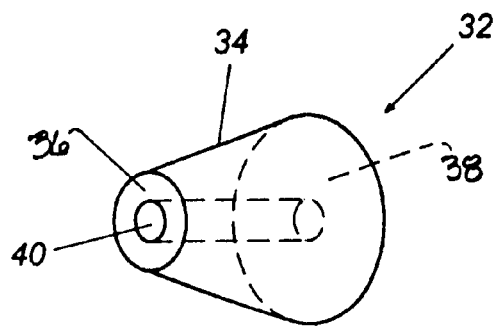
FIG. 4 is a perspective view of a preferred embodiment of a plug utilized in preferred embodiments of the present invention.

Reference will now be made in detail to the description of the present invention as illustrated in the drawings with like numerals indicating like parts throughout the several views. As shown in FIGS. 1 and 2, a preferred embodiment of the anchor 10 of the present invention incorporates an elongated body 12, which preferably is cylindrical in shape (although various other shapes may be utilized), with a proximal end 14 and a distal end 16. Preferably, the anchor is formed of a relatively non-reactive, durable material, such as stainless steel, titanium, etc. Although not necessary, distal end 16 preferably includes an anchor head 18, formed in a conventional hexagonal configuration, for instance, although various other configurations may be utilized and are considered well within the scope of the present invention, thereby allowing the anchor 10 to be conveniently driven into material of a skeletal member with the use of a driving tool (not shown), such as a screw driver, wrench, or drill incorporating a anchor-driving adapter, among others. In other embodiments, i.e., embodiments not incorporating external threads, for example (as described hereinafter), driving of the anchor may be accomplished with an impact tool, such as a mallet, impact wrench, etc.

Additionally, some embodiments of the body 12 include external threads 20, preferably formed along substantially the entirety of its length, although, in some embodiments, the external threads may be provided on less than substantially the entirety of the length of the anchor depending upon the particular application. In still other embodiments, no external threads are provided, although various other protrusions, ridges, or other friction-enhancing features and/ or surface treatments may be provided on the exterior of the anchor to facilitate secure engagement of the anchor within a skeletal member.

Body 12 also incorporates a passage 22 formed at least partially therethrough which preferably extends into the body from proximal end 14. In some embodiments, the passage 22 may be configured as a longitudinal bore, for instance. Passage 22 communicates with one or more fenestrations or dispersion holes 24, preferably formed at distal end 16, which are adapted for dispersing medical adhesive or boding cement 26 (i.e. methomathactuloid, cranial plast, etc.) from the anchor. Since cement 26 may produce an exothermic reaction during curing, holes 24 preferably are formed in the distal one-third of the anchor in order to reduce the possibility of thermal injury to nerve roots in the vicinity of the anchor. However, in embodiments utilizing non-exothermic reacting cement, the holes may be formed at various locations along the length of the anchor for dispersing the cement, as required, based upon the needs of the particular application.

As shown in FIG. 3, a preferred embodiment of anchor 10 is configured to be driven into a skeletal member, such as vertebral body 28. Depending upon the particular application, the skeletal member may be pre-drilled, thereby forming a anchor-receiving hole into which the anchor may be driven. Driving of the anchor may be accomplished in any suitable manner, including driving with the use of a driving tool as described hereinbefore. Preferably, after the anchor has been at least partially driven within the skeletal member, cement 26 is then delivered into passage 22, such as by injecting the cement with a syringe or other suitable delivery device, so that at least some of the cement is delivered through the passage 22, through the hole(s) 24, and out of the anchor. As the cement 26 passes out of the anchor, the cement preferably engages the various pores, concavities and interstices of the vertebral body 28, thereby creating a mass or collection 30 of cement about the anchor. After curing, the cement creates a firm fixation or anchoring of the anchor in the vertebral body.

Additionally, since the cement tends to engage the various pores, concavities and interstices of the skeletal member, the skeletal member may tend to be strengthened. Thus, the present invention has been found to be particularly useful for securely anchoring anchors within skeletal members of osteoporotic patients, for instance.

Figure 5:
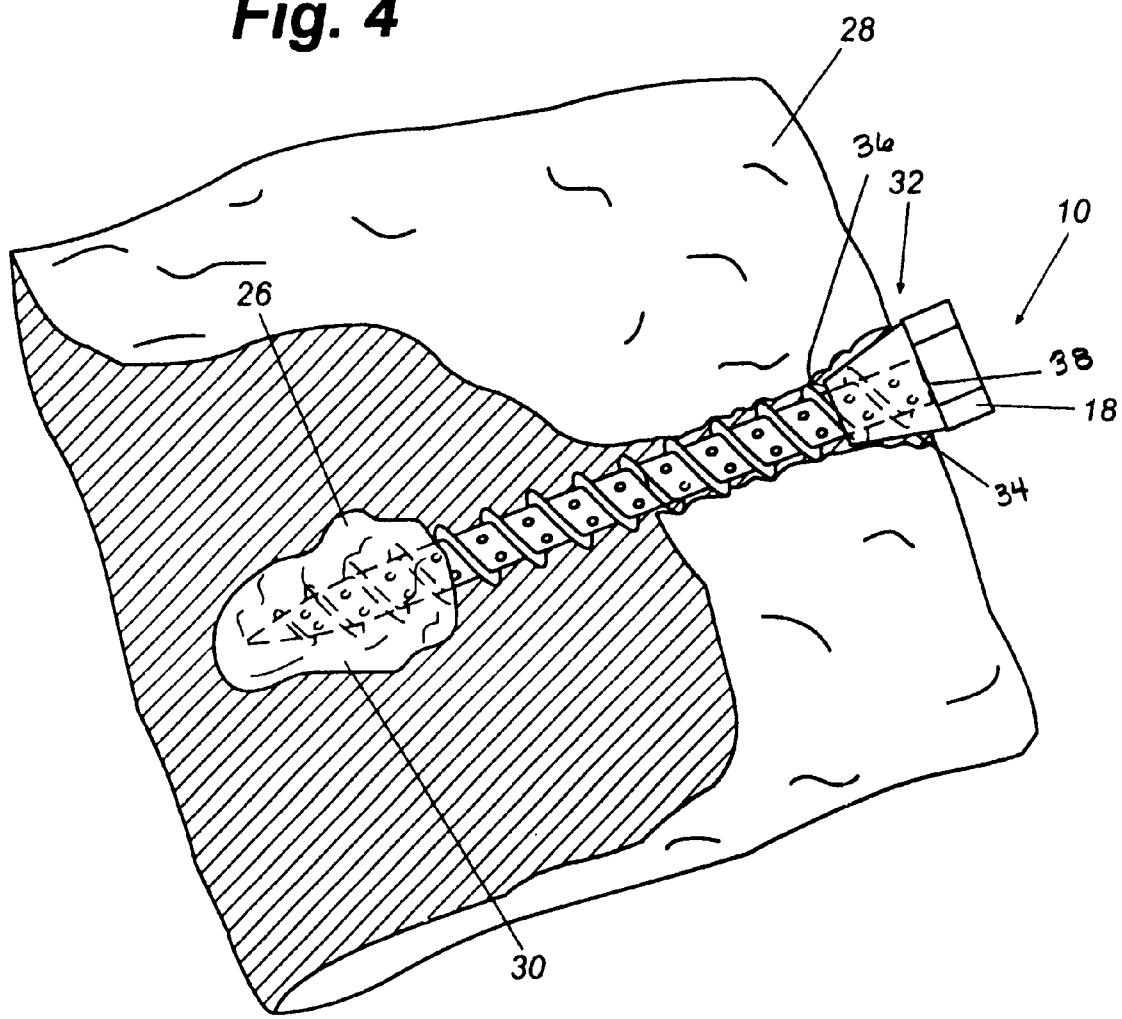
FIG. 5 is a partially cut-away perspective view of a preferred embodiment of the invention showed anchored within a representative skeletal member.

As depicted in FIG. 4, preferred embodiments of the anchor 10 may incorporate the use of a plug member 32 which is configured for securing the proximal end of the body 12 within a skeletal member. Preferably, plug member 32 is formed of a plastic or other semi-compliant material which may cooperate with the material of a skeletal member to substantially fix the position of the proximal end of the body within the skeletal member. Preferably, plug 32 incorporates a tapered side wall 34 which extends outwardly and downwardly from a first end wall 36 to a second end wall 38. Additionally, the plug member preferably incorporates a bore 40 extending through the first and second end walls which is sized and shaped to receive the body 12 of an anchor therethrough. So configured, plug member 32 may be received about the body of an anchor, with the anchor then being insertable into a skeletal member 28, such as depicted in FIG. 5. So positioned, the plug member 32 preferably engages the skeletal member at the proximal end of the anchor 10, thereby substantially preventing movement of the proximal end of the anchor relative to the skeletal member.

The foregoing description has been presented for purposes of illustration and description. It is not intended to be exhaustive or to limit the invention to the precise forms disclosed. Obvious modifications or variations are possible in light of the above teachings. The embodiment discussed, however, was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. A surgical anchor for anchoring within a vertebral body using bonding cement, said anchor comprising:

an elongated body having a proximal end and a distal end;

a passage extending at least partially through said body from said proximal end;

at least one hole extending at least partially through said body and communicating with said passage;

said passage and said at least one hole configured such that bonding cement is receivable in said passage at said proximal end, deliverable through said passage, through said at least one hole and into said vertebral body; and a plug member having first and second end walls and a side wall extending therebetween, said plug member being receivable about said elongated body such that said plug member is engagable with said vertebral body to substantially prevent movement of said proximal end of said elongated body relative to said vertebral body.

2. The surgical anchor of claim 1, wherein each of said at least one hole is formed along a distal most one-third of said elongated body.

3. The surgical anchor of claim 1, wherein said passage extends partially through said elongated body to define a partially cannulated surgical anchor.

4. The surgical anchor of claim 1, wherein said anchor is formed as a pedicle anchor configured to anchor within the vertebral body.

5. The surgical anchor of claim 1, wherein said elongated body has external threads formed along at least a distal end portion thereof, each of said at least one hole being arranged along a distal most one-third of said external threads.

6. The surgical anchor of claim 1, wherein said elongate body is substantially cylindrical in shape.

7. A method for anchoring a surgical anchor to a vertebral body, comprising:

provideing a surgical anchor having a proximal end, a distal end, an axial passage extending from the proximal end toward the distal end, and at least one lateral opening communicating with the axial passage, the surgical anchor including an enlarged proximal end portion;

inserting at least a portion of the surgical anchor into the vertebral body;

engaging the enlarged proximal end portion of the surgical anchor at least partially within the vertebral body to substantially prevent movement of the proximal end portion of the surgical anchor relative to the vertebral body; and delivering a bonding cement through the axial passage of the surgical anchor, through the at least one lateral opening and into the vertebral body.

8. The method of claim 7, wherein the enlarged proximal end portion of the surgical anchor is outwardly tapered in a proximal direction.

9. The method of claim 8, wherein the enlarged proximal end portion of the surgical anchor is defined by a plug member having opposite end walls, an outwardly tapered side wall, and an axial bore extending between the end walls; and further comprising positioning the surgical anchor within the axial bore of the plug member prior to the inserting.

10. The method of claim 7, wherein the axial passage extends partially through the surgical anchor; and wherein the delivering includes distributing the bonding cement entirely through the at least one lateral opening.

11. A system for anchoring a surgical anchor to a vertebral body; comprising:

a surgical anchor having a proximal end and a distal end, an axial passage extending from said proximal end toward said distal end, at least one lateral opening communicating with said axial passage, and an enlarged proximal end portion engagable within the vertebral body to substantially prevent movement of said proximal end portion relative to the vertebral body, said enlarged proximal end portion of the surgical anchor comprising a plug member having opposite end walls, a side wall, and an axial bore extending between said end walls that is sized and shaped to receive said surgical anchor therethrough; and a supply of bonding cement deliverable through said axial passage, out said at least one lateral opening and into the vertebral body.

12. The method of claim 11, wherein said side wall of said plug member is outwardly tapered in a proximal direction.

13. The system of claim 11, wherein said surgical anchor includes a head adapted to abut one of said end walls of said plug member to engage said plug member within the vertebral body.

14. The system of claim 11, wherein said axial passage extends partially through the surgical anchor such that said bonding cement is deliverable entirely through said at least one lateral opening.

15. The system of claim 11, wherein said bonding cement produces an exothermic reaction during curing; and wherein said surgical anchor defines external threads along substantially the entire length thereof, each of said at least one lateral opening is formed along a distal one-third of said external threads.

16. The system of claim 11, wherein said bonding cement produces an exothermic reaction during curing; and wherein each of said at least one lateral opening is formed along a distal one-third of the portion of the surgical anchor disposed within the vertebral body.

17. A system for anchoring a surgical anchor to a vertebral body; comprising:

a surgical anchor having a proximal end and a distal end, an axial passage extending from said proximal end toward said distal end, at least one lateral opening communicating with said axial passage, and an enlarged proximal end portion engagable within the vertebral body to substantially prevent movement of said proximal end portion relative to the vertebral body, said enlarged proximal end portion of said surgical anchor being formed of a semi-compliant material; and a supply of bonding cement deliverable through said axial passage, out said at least one lateral opening and into the vertebral body.

18. The system of claim 17, wherein said enlarged proximal end portion of said surgical anchor is formed of a plastic material.

* * * * *